United States Patent [19]

Robbins et al.

[11] 4,251,519

[45] Feb. 17, 1981

[54] PROCESS FOR THE PREVENTION AND REDUCTION OF ELEVATED BLOOD CHOLESTEROL AND TRIGLYCERIDES LEVELS

[75] Inventors: Ernest A. Robbins, High Ridge; Robert D. Seeley, Crestwood, both of Mo.

[73] Assignee: Anheuser-Busch, Incorporated, St. Louis, Mo.

[21] Appl. No.: 61,888

[22] Filed: Jul. 30, 1979

Related U.S. Application Data

[63] Continuation of Ser. No. 872,205, Jan. 25, 1978, abandoned, which is a continuation of Ser. No. 693,320, Jun. 7, 1976, abandoned.

[51] Int. Cl.$^3$ ..................... A61K 31/70; A61K 35/78
[52] U.S. Cl. ..................... 424/180; 424/195
[58] Field of Search ..................... 424/180, 195

[56] References Cited

U.S. PATENT DOCUMENTS

| | | | |
|---|---|---|---|
| 3,081,226 | 3/1963 | DiLuzio | 424/180 |
| 3,511,910 | 5/1970 | Halleck | 424/180 |
| 3,867,554 | 2/1975 | Sucher et al. | 426/60 |
| 3,887,431 | 6/1975 | Robbins et al. | 195/5 |

OTHER PUBLICATIONS

Chemical Abstracts, vol. 70: 65756r (1969) & vol 73:42508j (1970).
Kritchevsky et al., J. Food Sci. vol. 40, pp. 8–11, (1975).

*Primary Examiner*—Donald B. Moyer
*Attorney, Agent, or Firm*—Gravely, Lieder & Woodruff

[57] ABSTRACT

This application covers a process of lowering or preventing an increase in the level of cholesterol and triglycerides in the blood of humans and animals by including a yeast product or yeast fraction in the daily diet in an amount of up to 30% of the total food intake. The preferred additive is yeast glycan as described in U.S. Pat. No. 3,867,554.

4 Claims, No Drawings

PROCESS FOR THE PREVENTION AND REDUCTION OF ELEVATED BLOOD CHOLESTEROL AND TRIGLYCERIDES LEVELS

This is a continuation of application Ser. No. 872,205, filed Jan. 25, 1978; which is a continuation of Ser. No. 693,320 filed June 7, 1976, both now abandoned.

BACKGROUND OF THE INVENTION

This invention relates to a process for the partial or total prevention of an increase in the content of cholesterol and triglycerides in the blood of mammals (including man) receiving dietary cholesterol, and to a process for decreasing the content of cholesterol and triglycerides of mammals having elevated levels of cholesterol and triglycerides in the blood. Hereinafter when we speak of decreasing the concentration of blood cholesterol and triglycerides, we mean either or both of the foregoing.

More specifically, the process of this invention relates to the incorporation of yeast cells, fractured yeast cells, and fractions of yeast into the diet of mammals to partially or totally prevent an increase in blood cholesterol and triglycerides which normally occurs when cholesterol is incorporated into the diet. This process also relates to the reduction of the level of blood cholesterol and triglycerides in mammals having elevated blood cholesterol and triglycerides content.

The medical community regards elevated blood cholesterol and triglycerides as one of the major factors associated with increased risk of coronary heart disease in humans. The condition of elevated blood cholesterol and triglycerides is referred to as hypercholesterolemia and hyperlipidemia, respectively. Agents which prevent an increase or causes a decrease in blood cholesterol and triglycerides are called hypocholesterolemic and hypolipidemic agents, respectively.

Known dietary hypocholesterolemic agents may be divided into three classes according to their mode of action. One class is those compounds that inhibit endogenus synthesis of cholesterol. These compounds have the disadvantage of preventing the synthesis of cholesterol in those body tissues that need cholesterol. A second class is those compounds which inhibit the uptake of cholesterol in the intestine by competing with cholesterol for binding sites. A third class is those materials that interact with bile salts to prevent the recirculation of bile salts to the liver and thereby favor the increased excretion of cholesterol by its conversion to bile acids. It is generally believed that the hypocholesterolemic effect of many dietary fibers is due to their ability to interact with cholic acid, and that the decrease in the fiber content of the human dietary in this century may relate to the increase in coronary heart disease. The exact nature of the mechanism of the hypocholesterolemic effect of yeast and yeast fractions is not known at this time.

DETAILED DESCRIPTION

We have discovered that yeast cells, fractured yeast cells, and fractions of yeast, including yeast protein isolate, are hypocholesterolemic and hypolipidemic agents, when incorporated into an animal dietary. Those fractions that contain the cell walls of yeast are particularly effective. This effectiveness is fortuitous because the fractions containing the cell walls of yeast were developed for use as functional food ingredients for man. The process for obtaining the cell wall product, the composition, and food uses thereof are described in U.S. Pat. No. 3,867,554 issued on Feb. 18, 1975. We have called this product yeast glycan. Glycan is the isolated, comminuted cell walls of yeast. Glycan serves as a non-caloric thickener in liquid food systems at levels from 0.5% to greater than 10%. Furthermore, glycan imparts a fatty mouthfeel to liquid food systems that are devoid of fat, which is a recognized desirable attribute to those versed in the food art. Therefore, glycan can be incorporated into the human diet at sufficiently high levels to be effective in reducing blood cholesterol and triglycerides levels and still give a desirable food product. Furthermore, extensive testing has demonstrated the safety of glycan. Thus, glycan is safe to consume, efficacious as a hypocholesterolemic and hypolipidemic agent, and provides an organoleptically appealing food product.

As set forth in U.S. Pat. No. 3,867,554, the glycan, which is the preferred additive of this invention, comprises: yeast fragments and whole cells containing on a dry solids basis from about 5 to about 20% crude protein, from about 0.1 to about 3% nucleic acid, from about 0.1 to about 3% lipid, from about 0.5 to about 3% ash, and from about 60 to about 95 percent carbohydrate. The product has a minimum viscosity of 500 centipoise when suspended in a 10% aqueous suspension and the product has a majority of irregular cell wall fragments and a minor amount of whole cells containing a methylene blue stainable material. Preferably the product has a viscosity greater than 3,500 centipoise when suspended in a 10% aqueous suspension.

As mentioned, the glycan can be made by the process described in U.S. Pat. No. 3,867,554 or by the process of abandoned application of Robbins and Seeley Ser. No. 524,653 filed Nov. 18, 1974 entitled "A Process for the Manufacture of Yeast Glycan".

A protein isolate from bakers yeast also is surprisingly effective as a hypocholesterolemic agent. The process for obtaining this protein isolate, its composition, and the food uses thereof are described in U.S. Pat. No. 3,887,431 issued June 3, 1975. The protein isolate contains about 65-85% protein, (preferably 75%), about 7-15% lipid (preferably 10%), about 1-5% ash, (preferably 2%), and about 5-20% carbohydrate (preferably 12%) on a dry solids basis. The protein has a low nucleic acid content (preferably less than about 2%), is nutritious (PER=2.1), safe to consume, and useful in many food products. Thus, the protein isolate may be incorporated in foods to supply energy, nutritious protein, appealing texture and flavor in addition to providing means of controlling the level of serum cholesterol.

In this application when we refer to fractured yeast cells, we mean yeast cells whose walls have been ruptured or broken to an extent that the walls of the cell can be recovered devoid of cytoplasmic material.

In this application when we refer to residual yeast cells, we mean empty yeast cells, such as those commonly obtained after an autolysis process to produce autolyzed yeast extracts. During the autolysis process, the majority of the cytoplasmic material is self-digested and escapes through the cell wall to the surrounding medium. The cell wall of the residual yeast cells appears to maintain its integrity as determined microscopically. The residual yeast cells from the autolysis process is also called "autolysis residue" and contains about 21–35% protein, 1–5% ash, and 3–8% lipid on a dry basis.

The following examples illustrate the hypocholesterolemic and hypolipidemic effects of fractured yeast cells and yeast fractions as components of the diet. Young adult Sprague-Dawley strain albino rats were employed as test animals. The animals were individually housed in screen bottom cages in air-conditioned humidity controlled rooms. Feed and water were provided ad libitum.

The data of Example No. 1 show that the incorporation of glycan into a diet virtually devoid of cholesterol significantly reduces the serum cholesterol and triglycerides compared to an equal amount of non-nutritive-cellulose type fiber, such as Alpha-Cel. That is, the hypocholesterolemic and hypolipidemic effect observed in the diet containing glycan is not due to a reduction of sucrose in the diet, but is due to a glycan or yeast fraction effect per se. As may be seen, the cholesterol measurement in the blood after being fed the diet is not dependent on the amount of cholesterol in the foods which make up the diets. For example, Diet No. 1 contained less in the diet itself than Diet No. 3, but the blood of the rat fed Diet No. 3 has significantly less cholesterol than is in the blood of the rat fed Diet No. 1.

The data of Example No. 2 show that the incorporation of cholesterol and cholic acid into the diet markedly increases the serum cholesterol and triglycerides in male and female rats. This increase can be prevented by the addition of glycan to the diet. The amount of prevention is a function of the amount of glycan added.

The data of Example No. 3 shows that dried whole bakers yeast and dried fractured bakers yeast are hypocholesterolemic agents in that their incorporation into diets containing cholesterol and cholic acid prevent an increase in blood cholesterol. Whole cells, fractured cells, and glycan all contain the cell walls or fragmented cell walls of yeast.

The data of Example No. 4 show that the incorporation of cholesterol and cholic acid into the diet rapidly and markedly increases the serum cholesterol content, and that the addition of dried homogenate or glycan to the hypercholesterolemic diet rapidly and markedly prevents the increase. The data of Example No. 4 also show that the hypocholesterolemic potency is not related to the viscosity characteristic of glycan. A further surprising finding is that the dried protein isolate is a hypocholesterolemic agent.

The data of Example No. 5 show that the incorporation of glycan into the diet of animals having elevated serum cholesterol levels immediately decreases serum cholesterol despite the continued incorporation of cholesterol and cholic acid in the diet.

The data of Example No. 6 shows that brewers yeast, fractured brewers yeast, and fractions of brewers yeast added to the hypercholesterolemic diet of rats totally or partially prevents an increase in serum cholesterol. The data further show that the residual yeast cells (which are cell walls) are more effective than the fractured cells.

The data of Example No. 7 shows that C. utilis yeast, fractured C. utilis, and glycan therefrom are hypocholesterolemic agents. The glycan is particularly effective.

The data of Example No. 8 shows that the ingestion of glycan significantly lowers the serum cholesterol of a human subject who normally has elevated serum cholesterol. The data also strongly indicate a reduction in the triglycerides of this subject. The data strongly indicate a reduction in the serum cholesterol of the subject having normal serum cholesterol values.

Satisfactory fractured cells, glycan and protein isolates having hypocholesterolemic and hypolipidemic properties can be derived from not only the baker's yeast strains, such as Saccharomyces cerevisiae; but also from other food yeasts, such as brewer's yeast strains, such as Saccharomyces carlsbergensis; a lactose utilizing food yeast, Saccharomyces fragilis; and strains of Candida such as C. utilis. Saccharomyces fragilis has recently been reclassified to Kluyueromyces fragilis. It has further been discovered that the yeast products can be derived from these various strains of yeast which have been grown on a variety of media. The products from different strains vary in some degree in their composition, but all have the ability to decrease the cholesterol and triglycerides of humans as set forth in this invention.

When feeding whole yeast, the amount incorporated into the daily diet on a dry solids basis is up to about 30% and preferably is at least about 7% and more preferably at least about 10%. When feeding yeast glycan or fractured or residual cell walls the amount is at least about 2% and can be as much as 20% or ever 30%. When feeding protein isolate, the amount is at least about 5% and can be up to about 30%.

EXAMPLE NO. 1

The Effect of Dietary Glycan on Serum Cholesterol and Triglyceride of Rats Fed on Low Cholesterol Diets for Five Months Three diets were fed for a period of five months at which time a sample of whole blood was drawn by heart puncture from 10 males and 10 females in each diet group. The samples were centrifuged and cholesterol and triglyceride determinations were made on the serum fractions of each sample. All diets contained 20 parts of weight of casein, 8 parts corn oil, 4 parts Jones-Foster salts and 1 part of vitamin mix. In addition, diet No. 1 contained 62 parts sucrose and 5 parts non-nutritive fiber (Alpha-Cel). Diet No. 2 contained 47 parts of sucrose and 20 parts of non-nutritive fiber. Diet 3 contained 47 parts of sucrose and 20 parts of glycan. Analysis showed that the amounts of cholesterol contained in the ingredients of Diets 1, 2 and 3 were 2.87, 3.78 and 3.77 milligrams cholesterol per 100 grams of diet, respectively.

| Analysis of Blood Serum Sample After Five Months | | | | |
|---|---|---|---|---|
| | Male | | Female | |
| | cholesterol | triglycerides | cholesterol | triglyceride |
| Diet No. 1 | 129 ± 14[1] | 167 ± 33 | 116 ± 11 | 93 ± 35 |
| Diet No. 2 | 111 ± 10 | 140 ± 37 | 106 ± 13 | 63 ± 24 |
| Diet No. 3 | 101 ± 12* | 89 ± 17* | 98 ± 12 | 54 ± 19 |

Diet No. 2 vs. Diet 3
*Significant at $p = .05$
[1] The ± value is one standard deviation of the mean.

EXAMPLE NO. 2

The Effect of Levels of Dietary Glycan on Serum Cholesterol and Triglycerides of Rats Receiving Dietary Cholesterol Seven diets were fed. All diets contained 20 parts by weight casein, 8 parts corn oil, 4 parts salts, and 1 part vitamin mix. The remaining ingredients are noted. After four weeks, whole blood was drawn by heart puncture from 10 males and 10 females in each diet group. The sample was centrifuged and cholesterol and triglyceride determinations were made on the serum fraction.

| Ingredients (%) | DIETS | | | | | | |
|---|---|---|---|---|---|---|---|
| | 1 | 2 | 3 | 4 | 5 | 6 | 7 |
| Non-nutritive fiber | 2 | 2 | 20 | — | — | — | — |
| Sucrose | 65 | 63.8 | 45.8 | 63.8 | 60.8 | 55.8 | 45.8 |
| Glycan | — | — | — | 2 | 5 | 10 | 20 |
| Cholesterol | — | 1 | 1 | 1 | 1 | 1 | 1 |
| Cholic-acid | — | 0.2 | 0.2 | 0.2 | 0.2 | 0.2 | 0.2 |
| Blood Serum Analysis After Five Months | | | | | | | |
| Males: | | | | | | | |
| Cholesterol (mg%) | 96 | 137 | 151 | 145 | 124 | 122** | 90** |
| Triglycerides (mg%) | 227 | 217 | 249 | 214 | 172* | 199 | 150** |
| Females: | | | | | | | |
| Cholesterol (mg%) | 100 | 174 | 193 | 170 | 150* | 122** | 89** |
| Triglycerides (mg%) | 95 | 112 | 81 | 78 | 59 | 68 | 64 |

*Significant (p = 0.05) versus Diet 2
**Significant (p = 0.01) versus Diet 2
(The foregoing Example No. 2 shows that when rats are fed cholesterol and cholic-acid, the addition of glycan to the diet significantly reduces cholesterol and triglycerides content of the blood)

EXAMPLE NO. 3

The Hypocholesterolemic Effect of Whole Bakers Yeast, Fractured Bakers Yeast, and Glycan in Rat Diets Dried bakers yeast, dried fractured bakers yeast[1], and glycan were incorporated into the diet of rats. Six diets were fed. All diets contained 18% protein. In addition to the noted ingredients, all diets contained 8% corn oil, 4% salts, and 1% vitamin mix. After four weeks, whole blood was drawn by heart puncture from 10 males and 10 females in each diet group. The sample was centrifuged and cholesterol was determined on the serum fraction.

[1]Fractured bakers yeast was prepared by repeated passage of a yeast slurry through a high-pressure (9000 psi) homogenizer, followed by spray drying.

| Ingredients (%) | DIETS | | | | | | |
|---|---|---|---|---|---|---|---|
| | 1 | 2 | 3 | 4 | 5 | 6 | 7 |
| Non-nutritive fiber | 2 | 2 | — | — | — | — | — |
| Cholesterol | — | 1 | 1 | 1 | 1 | 1 | 1 |
| Cholic-acid | — | 0.2 | 0.2 | 0.2 | 0.2 | 0.2 | 0.2 |
| Casein | 20 | 20.0 | 3.3 | 3.3 | 11.7 | 20 | 20 |
| Sucrose | 65 | 63.8 | 52.5 | 52.5 | 59.1 | 60.8 | 63.8 |
| Dried Whole Yeast | — | — | 30 | — | — | — | — |
| Dried Yeast Homogenate | — | — | — | 30 | 15 | — | — |
| Glycan | — | — | — | — | — | 5 | 2 |
| Blood Serum Analysis After Four Weeks | | | | | | | |
| Cholesterol (mg%) | | | | | | | |
| Males | 92 | 169 | 96* | 94* | 105* | 127* | 140** |
| Females | 87 | 276 | 98* | 80* | 142* | 171* | 281 |

*Significantly (p = .01) different from Diet 2
**P = .05

EXAMPLE NO. 4

Hypocholesterolemic Effect of Fractions of Bakers Yeast in Rat Diets

An homogenate of bakers yeast (fractured bakers yeast) was fractionated into glycan, a protein isolate with reduced Nucleic acid content, and an extract as described in U.S. Pat. Nos. 3,867,554 and 3,887,431 and application Ser. No. 349,316 now U.S. Pat. No. 3,914,450 issued Oct. 21, 1975.

Seven diets were fed. All diets contained 18% protein (consisting of the test material and casein) 8% corn oil, 4% salts and 1% vitamin mix. The remaining ingredients are noted. At weekly intervals for four weeks whole blood was drawn from the caudal vein from 10 male rats in each diet group. The sample was centrifuged and cholesterol was determined on the serum fraction.

| Diet | Diet Composition, % | | | | | | |
|---|---|---|---|---|---|---|---|
| | 1 | 2 | 3 | 4 | 5 | 6 | 7 |
| Sucrose | 65 | 63.8 | 59.3 | 63.0 | 57.2 | 51.8 | 51.8 |
| Casein | 20 | 20 | 12.5 | 8.8 | 14.6 | 20 | 20 |
| Corn Oil | 8 | 8 | 8 | 8 | 8 | 8 | 8 |
| Vitamin & Salts | 5 | 5 | 5 | 5 | 5 | 5 | 5 |
| Cholesterol | — | 1 | 1 | 1 | 1 | 1 | 1 |
| Cholic Acid | — | 0.2 | 0.2 | 0.2 | 0.2 | 0.2 | 0.2 |
| Alpha Cel | 2 | 2 | — | — | — | — | — |
| Dried Yeast Homogenate | — | — | 15 | — | — | — | — |
| Dried Protein Isolate | — | — | — | 15 | — | — | — |
| Dried Extract Fraction | — | — | — | — | 15 | — | — |
| Glycan (R4604) 3400 cps | — | — | — | — | — | 15 | — |
| Glycan (R4605) 1500 cps | — | — | — | — | — | — | 15 |
| Blood Serum Analysis | | | | | | | |
| Serum Cholesterol mg% 0 Wk. | 85 | 82 | 87 | 81 | 87 | 86 | 85 |
| 1 Wk. | 97 | 128 | 114* | 108* | 132 | 88** | 90** |
| 2 Wk. | 90 | 150 | 110* | 117* | 185* | 95** | 88** |
| 3 Wk. | 88 | 154 | 119** | 110** | 133 | 102** | 101** |

(1) 8% w/v suspensions of Glycan R4604 and R4605 had viscosities of 34000 cps 1500 cps respectively.
*Significant when p = 0.05;
**when p = 0.01 from Diet 2

EXAMPLE NO. 5

The Ability of Dietary Glycan to Lower Elevated Blood Cholesterol in the Rat

The 10 rats that had received Diet #1 for 4 weeks in Example 4 were maintained on Diet #1 for an additional 4 weeks. The 10 rats that has received Diet #2 for 4 weeks in Example 4 were divided into two groups of five each, which are called 2A and 2B. The five rats of group 2A continued to receive Diet #2 for four weeks. The five rats of group 2B were switched to Diet #7 and received Diet #7 for four weeks. At weekly intervals for four weeks, whole blood was drawn from the caudal vein of each rat for the determination of serum cholesterol.

| | Blood Analysis | | | |
|---|---|---|---|---|
| Group | | #1 | 2A | 2B |
| Diet | | #1 | #2 | #7 |
| Cholesterol (mg%) | 0 week | 96 | 157 | 157* |
| | 1 week | 96 | 148 | 115** |
| | 2 weeks | 96 | 156 | 99** |
| | 3 weeks | 96 | 148 | 115** |
| | 4 weeks | 103 | 133 | 111** |

*Significantly different (p = .01) from Group #1
**Significantly different (p = .01) from Group 2A. Not significantly different from Group #1.

EXAMPLE NO. 6

Hypocholesterolemic Effect of Whole Brewers Yeast, Fractured Brewers Yeast and Brewers Yeast Fractions in Rat Diets Dried brewers yeast (as recovered from the manufacture of beer and dried), fractured brewers yeast[1], autolyzed yeast extract[2], and residual yeast cells[2] were incorporated into the diet of male rats. All diets contained 18% protein. In addition to the noted ingredients, all diets contained 8% corn oil, 4% salt, 1% vitamin mix. After four weeks, whole blood was drawn by heart puncture. The sample was centrifuged and cholesterol was determined in the serum fraction. The following table entitled "DIETS" gives the results of this work.

[1]Fractured brewers yeast was prepared by repeated passage slurry through a high-pressure (9000 psi) homogenizer, followed by spray drying.

[2]A suspension of undried brewers yeast containing 10% dry solids was incubated at 40° C. for 48 hours in the presence of 1% ethylacetate. The suspension was then centrifuged to obtain the residual yeast extract, which was then concentrated in vacuo. The residual yeast cells and the concentrated autolyzed yeast extract were spray dried.

| Ingredients (%) | 1 | | 2 | | 3 | 4 | 5 | 6 | 7 | 8 | 9 |
|---|---|---|---|---|---|---|---|---|---|---|---|
| Non-nutritive Fiber | 2 | | 2 | | — | — | — | — | — | — | — |
| Cholesterol | — | | 1 | | 1 | 1 | 1 | 1 | 1 | 1 | 1 |
| Cholic Acid | — | | .2 | | .2 | .2 | .2 | .2 | .2 | .2 | .2 |
| Casein | 20 | | 20 | | 1 | 11 | 14 | 15 | 19 | 1 | 11 |
| Sucrose | 65 | | 63.8 | | 54.8 | 59.8 | 61.8 | 55.8 | 51.8 | 54.8 | 59.8 |
| Test No.: | 508 | 537 | 508 | 537 | 537 | 537 | 537 | 537 | 537 | 508 | 508 |
| Dried Brewers Yeast | — | — | — | — | 30 | 15 | 10 | — | — | — | — |
| Dried Fractured Brewers Yeast | — | — | — | — | — | — | — | — | — | 30 | 15 |
| Residual Yeast Cells | — | — | — | — | — | — | — | 15 | — | — | — |
| Autolyzed Yeast Extract | — | — | — | — | — | — | — | — | 15 | — | — |
| Blood Serum Analysis: | | | | | | | | | | | |
| Cholesterol (mg%) | 91 | 112 | 156 | 179 | 103 | 138 | 150 | 123 | 148 | 93 | 116 |
| Elevation from Diet #1 (mg%) | | | 65 | 67 | −9 | 26 | 38 | 11 | 36 | 2 | 25 |
| Prevention of Increase (%) | | | | | 113 | 61 | 57 | 84 | 46 | 97 | 62 |

EXAMPLE NO. 7

Hypocholesterolemic Effect of Whole Cells, Fractured Cells, and Glycan from *Candida utilis*

*Candida utilis* cells were prepared and fractured in accordance with Examples of U.S. Pat. No. 3,867,554 and dried. Glycan then was prepared according to the disclosure of U.S. Pat. No. 3,867,554.

All diets contained 18% protein, 8% corn oil, 4% salt, and 1% vitamin mix. The remaining ingredients are noted. After four weeks, whole blood was drawn by heart puncture. The sample was centrifuged and cholesterol was determined on the serum fraction.

| Ingredients (%) | 1 | 2 | 3 | 4 | 5 | 6 |
|---|---|---|---|---|---|---|
| Non-nutritive Fiber | 2 | 2 | — | — | — | — |
| Cholesterol | — | 1 | 1 | 1 | 1 | 1 |
| Cholic Acid | — | .2 | .2 | .2 | .2 | .2 |
| Casein | 20 | 20 | 4 | 12 | 13 | 17 |
| Sucrose | 65 | 63.8 | 51.8 | 58.8 | 57.8 | 53.8 |
| Dried *C. utilis* cells | — | — | 30 | 15 | — | — |
| Dried fractured *C. utilis* cells | — | — | — | — | 15 | — |
| Dried Glycan - *C. utilis* | — | — | — | — | — | 15 |
| Blood Serum Analysis: 4 Weeks: | | | | | | |
| Cholesterol (mg%) | 112 | 179 | 117 | 155 | 123 | 79 |

EXAMPLE NO. 8

Hypocholesterolemic Effect of Glycan in Humans

One subject (RDS) with a history of elevated serum cholesterol ingested Bakers Yeast Glycan (25 grams suspended in one pint of water three times per day) in addition to his usual diet for a period of 56 days followed by a period of 90 days without ingesting the Glycan but continuing with his usual diet. Serum cholesterol and triglycerides were measured several times during the tests after fasting overnight.

One subject (EAR) with a history of normal serum cholesteril ingested Bakers Yeast Glycan (25 grams suspended in one pint of water two times per day) in addition to his usual diet for a period of 78 days followed by a period of 71 days without ingesting the Glycan, but continuing with his usual diet. Serum cholesterol and triglycerides were measured several times during the tests after fasting overnight.

| SUBJECT (RDS) | | | | | |
|---|---|---|---|---|---|
| Serum Analysis (mg%) | | | Serum Analysis (mg%) | | |
| Days Test Diet | Cholesterol | Triglycerides | Days Basal | Cholesterol | Triglycerides |
| | | | 21 | 257 | — |
| 23 | 243 | 62 | 24 | 237 | 84 |
| 28 | 221 | 23 | 28 | 265 | 75 |
| 30 | 184 | 69 | 35 | 246 | 85 |
| 34 | 218 | 75 | 55 | 240 | 97 |
| 37 | 216 | 63 | 63 | 257 | 67 |
| 44 | 250 | 56 | 70 | 264 | 80 |
| 47 | 240 | 53 | 77 | 241 | 202 |

-continued

SUBJECT (RDS)

| Serum Analysis (mg%) | | | Serum Analysis (mg%) | | |
|---|---|---|---|---|---|
| Days Test Diet | Cholesterol | Triglycerides | Days Basal | Cholesterol | Triglycerides |
| 51 | 226 | 109 | 87 | 242 | 65 |
| 56 | 217 | 55 | 91 | 258 | 72 |
| Average | 224[a] n | 63[b] | Average | 251[a] | 78[b] |

[a]Significantly different (p = .005)
[b]Significantly different (p = .1)

SUBJECT (BAR)

| Serum Analysis (mg%) | | | Serum Analysis (mg%) | | |
|---|---|---|---|---|---|
| Days Test Diet | Cholesterol | Triglycerides | Days Basal | Cholesterol | Triglycerides |
| 31 | 143 | 36 | 8 | 175 | 52 |
| 37 | 181 | 102 | 15 | 170 | 67 |
| 45 | 165 | 31 | 22 | 167 | 67 |
| 50 | 150 | 60 | 50 | 171 | 69 |
| 57 | 174 | 46 | 64 | 186 | 48 |
| 64 | 152 | 50 | 71 | 180 | 46 |
| 71 | 140 | 48 | Average | 175[c] | 58 |
| 78 | 174 | 55 | | | |
| Average | 160[c] | 54 | | | |

[c]Significantly different (p = .07)

What is claimed is:

1. A process of decreasing the concentration of blood cholesterol and triglycerides in mammals in need thereof comprising the oral administration to mammals in need thereof of yeast glycan resulting from comminuting yeast cell walls, said glycan having a major portion of yeast cell wall fragments and a minor portion of whole cells and containing on a dry solids basis 5-20% crude protein, 0.1-3% nucleic acid, 0.1-3% liquid, 0.5-3% ash and 60-95% carbohydrate, and having a viscosity of greater than 500 cp when suspended in a 10% aqueous solution.

2. The process of claim 1 wherein the yeast glycan comprises at least 2% of the daily dietary intake on a dry basis.

3. A process according to claim 1 whereby the yeast glycan constitutes up to 20% of the daily dietary intake on a dry basis.

4. The process of claim 1 wherein the yeast glycan is produced by homogenization of whole yeast cells.

* * * * *